United States Patent
Yamamoto et al.

(10) Patent No.: US 7,560,074 B2
(45) Date of Patent: Jul. 14, 2009

(54) INSTRUMENT AND METHOD FOR BREAKING-UP SAMPLE

(75) Inventors: Takuji Yamamoto, Adachi-ku (JP); Yuko Ushiki, Adachi-ku (JP); Shunji Hattori, Adachi-ku (JP); Shinkichi Irie, Adachi-ku (JP)

(73) Assignee: Nippi, Inc., Tokyo (JP)

( * ) Notice: Subject to any disclaimer, the term of this patent is extended or adjusted under 35 U.S.C. 154(b) by 750 days.

(21) Appl. No.: 10/527,094

(22) PCT Filed: Dec. 17, 2004

(86) PCT No.: PCT/JP2004/019453

§ 371 (c)(1), (2), (4) Date: Mar. 9, 2005

(87) PCT Pub. No.: WO2005/085800

PCT Pub. Date: Sep. 15, 2005

(65) Prior Publication Data

US 2006/0078474 A1    Apr. 13, 2006

(30) Foreign Application Priority Data

Mar. 2, 2004    (JP)    .................... 2004-057108

(51) Int. Cl.
*B01L 11/00*    (2006.01)
*B01L 3/00*    (2006.01)
*C12M 1/34*    (2006.01)

(52) U.S. Cl. .................. 422/101; 422/99; 435/288.1

(58) Field of Classification Search ............... None
See application file for complete search history.

(56) References Cited

U.S. PATENT DOCUMENTS

| 4,683,058 A | 7/1987 | Lyman et al. |
| 6,221,655 B1 | 4/2001 | Fung et al. |
| 2004/0005608 A1 | 1/2004 | Saghbini |

FOREIGN PATENT DOCUMENTS

WO    02088296 A    11/2002

OTHER PUBLICATIONS

EPO Office Action dated Oct. 8, 2007.

(Continued)

*Primary Examiner*—Jill Warden
*Assistant Examiner*—Timothy G Kingan
(74) *Attorney, Agent, or Firm*—Browdy and Neimark, P.L.L.C.

(57) ABSTRACT

The present invention provides a sample breaking-up instrument and a method thereof, in which a pressing member is pressed by a centrifugal force against a sample within a cylindrical body provided with a filter member to thereby break-up the sample safely and efficiently. Provided is an instrument for breaking-up a sample, comprising: a cylindrical body having a through hole opening in both ends thereof; a filter member installed in one end of the cylindrical body within the through hole; and a pressing member to be operatively inserted into the hole of the cylindrical body from the other end thereof so as to be slidable therethrough in a sealed manner, wherein a force is exerted on the pressing member so that the pressing member presses the sample placed between the pressing member and the filter member against the filter member and thereby the sample is forced to pass through the filter member and is thus broken-up.

5 Claims, 5 Drawing Sheets

OTHER PUBLICATIONS

Asone Co. Ltd., Catalog: (potter-type homogenizer), "Comprehensive equipment catalog for research and development 700000, 2001→2003". (Nov. 2001), p. 944. and Abstract from Fisher Catalog: Homogenizers: "Wheaton Potter-Elvehjem Tissue Grinders". [online], [retrieved May 30, 2005]. Retrieved from Fisher Scientific, <URL:http:/www1.fishersci.com/>.

Asone Co., Ltd., Catalog: (homogenizer of rotor-stator system), "Comprehensive equipment catalog for research and development 700000, 2001→2003". (Nov. 2001), p. 944 and Abstract from Fisher Catalog: Homogenizers: "Ultra-Turrax T25 Homogenizer". [online], [retrieved May 30, 2005]. Retrieved from Fisher Scientific, <URL:http:/www1.fishersci.com/>.

Asone Co., Ltd., Catalog: (ball mill) "Comprehensive equipment catalog for research and development 700000, 2001→2003". (Nov. 2001), p. 946.

Qiagen Co., Product Guide: (QIA shredder) "QIAGEN product guide 2004". (2003). p. 258 and Abstract from QIAGEN.com [online], [retrieved May 30, 2005]. Retrieved from <url:http:/www1.qiagen.com/products/accessories/QIAshredder.aspx?showinfo=1&P...>.

Kinematica AG, Catalog: Polytron PT 1300 D Digital- handheld disperser) "Polytron Dispersing and mixing technology by Kinematica".

Kinematica AG, Catalog: Polytron PT 2100 D Digital- handheld disperser) "Polytron Dispersing and mixing technology by Kinematica".

Retsch, Catalog: (Ball mills) :Size reduction and homogenization with ball mills.

RNEASY Mini Handbook (Third Edition), QIAGEN Distributors, Jun. 2001. XP-002331631.

EPO Office Action dated Oct. 8, 2007.

INSTRUMENT AND METHOD FOR BREAKING-UP SAMPLE

TECHNICAL FIELD

The present invention relates to an instrument and a method for breaking up a sample safely and efficiently, and more specifically to a sample breaking-up instrument and method in which a pressing member is pressed by a centrifugal force against a sample within a cylindrical body provided with a filter member to thereby break-up the sample safely and efficiently.

BACKGROUND ART

In a broad range of fields of physics and chemistry, research based on sample analysis is an essential and important process. It is an especially critical process in biology, particularly in the research of pharmaceuticals and diagnostic medicines for both humans and animals. To analyze a sample, it is firstly required "to break-up" and then "to homogenize" the sample. Especially in a case of a biological sample, when it is used for extracting protein or preparing RNA, DNA for PCR analysis, it is required to break-up its structural base, such as cell membrane, cell wall and the like, physically (mechanically) or chemically. The term "to break-up" used herein implies "to destroy tissue and/or cells of a sample physically (mechanically)", and the term "to homogenize" implies "to destroy tissue and/or cells of a sample physically (mechanically), and then to add a buffer solution to the resultant substance in a suitable manner so as to produce a suspension thereof".

A conventional breaking-up method includes those using such instruments as a potter-type homogenizer (see, for example, "Comprehensive equipment catalog for research and development 70000, 2001→2003" Asone Co., Ltd, November 2001, p. 944"), a homogenizer of rotor-stator system (see, for example, "Comprehensive equipment catalog for research and development 70000, 2001→2003" Asone Co., Ltd, November 2001, p. 944"), and a ball mill (see, for example, "Comprehensive equipment catalog for research and development 70000, 2001→2003" Asone Co., Ltd, November 2001, p. 946").

However, in the breaking-up methods as mentioned above, heat is generated, and the heat could modify the sample (could cause damage to characteristics inherent to the sample). Consequently, there is a risk that an analysis reflecting the action and structure in vivo could not be any more obtained (especially, polymer components, such as protein, nucleic acid and polysaccharide, are required to be homogenized in conditions free from possible modification caused by heat). Further, in the conventional breaking-up methods, if a number of samples is increased, the instruments used need to be cleaned to avoid mixing among the samples (since those homogenizers are expensive and thus not "disposable", they have to be used multiple times, cleaning them after each use).

In addition, especially in the potter-type homogenizer and the rotor-stator system homogenizer, since their operations are carried out in an open system, there could be a fear of contamination of the surroundings.

On one hand, one conventional breaking-up method that can solve the problem of modification of the sample due to the generated heat and the problem of contamination of the surroundings has employed the QIA shredder manufactured by QIAGEN to break-up the sample (see, for example, "QIAGEN Product Guide 2004" QIAGEN Co., Ltd, 2003, p. 258"). This method is characterized in that a centrifugal force is used to press the sample against a filter in the QIA shredder to thereby force the sample to pass through the filter and to be broken-up.

DISCLOSURE OF THE INVENTION

Problem to be Solved by the Invention

However, in the breaking-up method using the QIA shredder, since the centrifugal force only acts on the sample itself, a force pressing the sample against the filter is small. Thus, according to this method, the breaking-up efficiency is low as compared to other conventional breaking-up methods, and this method is problematically only applicable to limited samples.

An object of the present invention is to provide a sample breaking-up instrument that is inexpensive and disposable and a sample breaking-up method, which can solve both of the above-described problems of modification of the sample due to generated heat and contamination of the surroundings.

Another object of the present invention is to provide a sample breaking-up instrument and a sample breaking-up method, allowing for relatively hard samples, such as brain tissue, liver tissue and the like, to be broken-up efficiently.

Means to Solve Problem and Effect Thereof (1) According to a first aspect of the present invention, in order to solve the above-described problem, there is provided an instrument for breaking-up a sample comprising a cylindrical body having a through hole opening in both ends thereof, a filter member installed in one end of said cylindrical body within said through hole, and a pressing member to be operatively inserted into said hole of said cylindrical body from the other end thereof so as to be slidable therethrough in a sealed manner, wherein a force is exerted on said pressing member so that said pressing member presses said sample placed between said pressing member and said filter member against said filter member and thereby said sample is forced to pass through said filter member and is thus broken-up.

Therefore, according to a sample breaking-up instrument of the present invention, owing to its simple structure, advantageously there will be obtained such effects that a manufacturing cost can be reduced, the instrument can be made disposable, and mixing among the samples, which could occur when the same instrument is used to "break-up" a plurality of samples, can be prevented.

Further, since the pressing member is sealingly inserted into the hole of the cylindrical body, other effects can be obtained that the back-flow of the sample can be prevented, so that the safety of an operator may be ensured and also contamination to the surrounding environment may be prevented.

Still further, since force is exerted on the pressing member when the sample is forced to pass through the filter member, advantageously the "breaking-up" efficiency of the sample can be improved.

(2) Preferably, the force to be exerted on said pressing member is a centrifugal force.

Accordingly, since the commercially available centrifuge can be used when a sample is "broken-up" by a sample breaking-up instrument of the present invention, the process can be simplified and also a plurality of samples can be "broken-up" all at once, thus advantageously bringing about an effect of improving working efficiency.

(3) Further, preferably said pressing member is provided with a protrusion extending radially on an end surface thereof to face to the sample wherein said pressing member is able to be pressed while being rotated with respect to said filter member so that said sample may be mashed before being forced to pass through said filter member by said force.

Thus, since the sample is mashed beforehand, advantageously there will be an effect that "breaking-up efficiency" of a sample (especially, a relatively hard sample, such as brain tissue and liver tissue) can be improved.

(4) Further advantageously, said pressing member is provided with a groove extending circumferentially on an outer surface thereof in the vicinity of its top end located in the sample side, and an O-ring is fitted in said groove.

Accordingly, it will bring about an effect advantageously that the pressing member can reliably seal the hole of the cylindrical body.

(5) Further preferably, said filter member has a plurality of through holes, each having a diameter of a cross section orthogonal to an axis in a range of 50 to 200 micrometers.

Accordingly, it will bring about an effect that a desired sample can be "broken-up".

(6) Yet preferably, said filter member defines a plate having a thickness in a range of 1 to 3 millimeters. Accordingly, it will bring about an effect that a desired sample can be "broken-up", and also a filter member has a desired strength.

(7) Still preferably, said cylindrical body is provided with a drop-out stop for preventing said filter member from dropping out of the cylindrical body, in the vicinity of the opening located in said one end thereof.

Therefore, when the sample is "broken-up", it will bring about an effect that the filter member is prevented from dropping out of said cylindrical body.

(8) According to a second aspect of the present invention, in order to solve the above-described problem, there is provided a method for breaking-up a sample comprising the steps of:

preparing a cylindrical body equipped with a filter member in one end of a through hole formed therein so as to open in both ends;

placing said sample into said hole of said cylindrical body from the other opening end thereof;

operatively inserting a pressing member into said hole of said cylindrical body from said other opening end thereof so as to be slidable therethrough in a sealed manner; and exerting a centrifugal force on said pressing member so that said pressing member may press said sample against said filter member to thereby force said sample to pass through said filter.

An effect to be brought about from this method is substantially similar to those described in said (1) and (2).

(9) Preferably, said pressing member is provided with a protrusion extending radially on an end surface thereof so as to face the sample, and said method further comprises a step of mashing said sample by pressing said pressing member while rotating it with respect to said filter member before exerting centrifugal force on said pressing member.

An effect to be brought about from this method is substantially similar to that described in said (3).

BEST MODE FOR CARRYING OUT THE INVENTION

An embodiment of a sample breaking-up instrument according to the present invention will now be described with reference to FIGS. 1 through 5.

Figure 1:
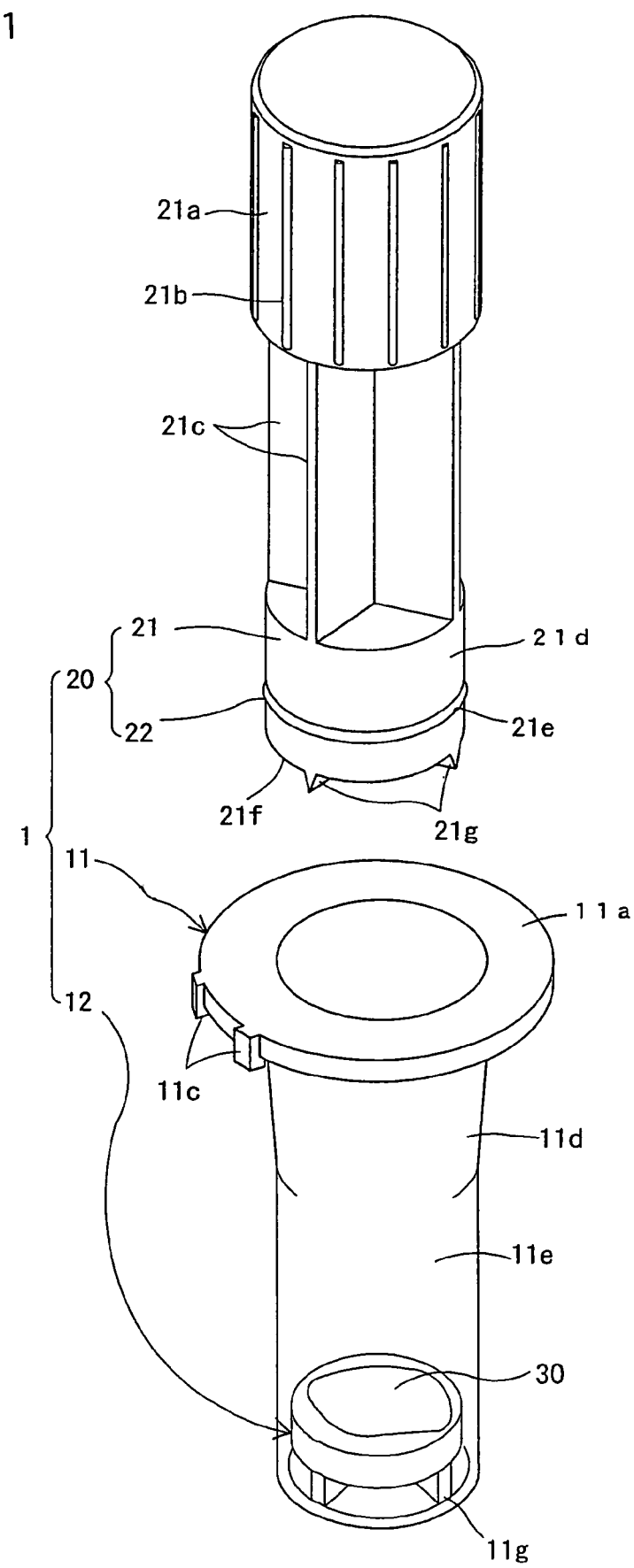
FIG. 1 is an exploded perspective view of a sample breaking-up instrument to illustrate an embodiment of a sample breaking-up instrument according to the present invention (First embodiment)

In FIG. 1, the sample breaking-up instrument 1 substantially comprises a cylindrical body or a breaking-up tube 11, a filter member or a filter 12 and a pressing member or a breaking-up stick 20.

In FIG. 1, the breaking-up tube 11 defines substantially a cylindrical body of integrally molded type (e.g., injection molded) from plastic, comprising a tapered section 11d and a cylindrical section 11e extending from one end of said tapered section 11d located in its contracted diameter side, said tube 11 having a through hole opening in both ends (openings 11b and 11f). In this illustrated embodiment, the tapered section 11d has been arranged in the breaking-up tube 11 to facilitate an inserting operation of the breaking-up stick 20 into the breaking-up tube 11. Further, preferably the breaking-up tube 11 is transparent (clear or colored) so that a sample 30 placed inside thereof can be visually recognized, but if the sample 30 has a characteristic of being modified by a light, it may be opaque so as to block the external light.

Figure 3:
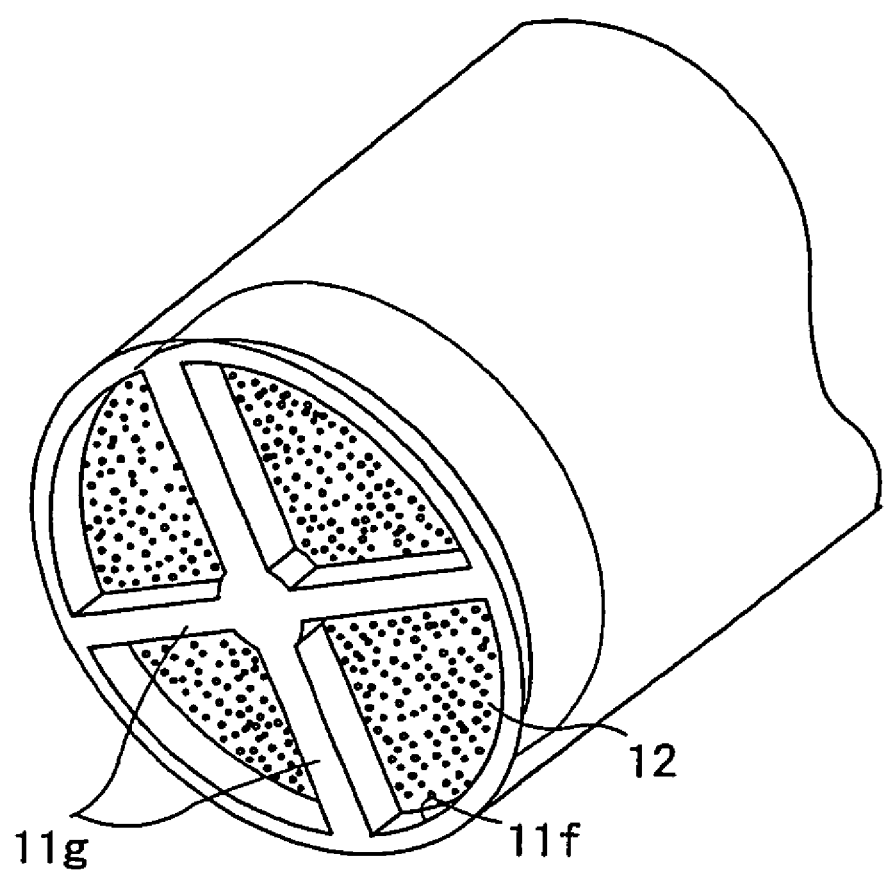
FIG. 3 is a perspective view of a bottom portion of a cylindrical body in FIG. 1 (First embodiment)

A ring-shaped flange 11a is arranged on the other end of the tapered section 11d located in an enlarged diameter side (an upper end portion in FIG. 1), and two claw-shaped fixing sections 11c are disposed on a periphery of the flange 11a, which are spaced by a certain distance from each other and extend downward. A lower end opening 11f of the cylindrical body 11e is provided with two plate-like drop-out stops 11g extending in diametrical directions so as to cross at right angles with each other, as shown in FIG. 3. The drop-out stop 11g prevents the filter 12 from dropping out when the sample 30 is broken-up. It is to be noted that the drop-out stop 11g may have other configuration including, for example, a protrusion extending inward in the radial direction (not shown) or even the drop-out stop may not be provided. It is to be noted that the breaking-up tube 11 may be made of other material. Further, the breaking-up tube 11 may be a cylindrical body having no tapered section 11d and/or may have no flange 11a.

The disc-like filter 12 has an outer diameter slightly larger than an inner diameter of the cylindrical section 11e and is fitted fixedly to an inner surface of the cylindrical section 11e above the drop-out stop 11g. The filter 12 is a commercially available hard filter made of polypropylene or glass having a thickness in a range of 1 mm to 3 mm provided with a number of substantially spherical holes having a diameter in a range of 50 to 200 micrometers. Thereby, the filter 12 is provided with a number of through holes each having a diameter in a range of 50 to 200 micrometers when measured in the plane-orthogonal to a longitudinal axis of the cylindrical section 11e. It is to be noted that if the filter 12 is made of polypropylene, it may employ a filter manufactured by POREX Corp. in Germany, for example, and alternatively if the filter 12 is made of glass, then it may employ a filter manufactured from SIBATA SCIENTIFIC TECHNOLOGY LTD., for example, on which a detailed explanation should be herein omitted. It is a matter of course that the filter 12 may employ other configurations and materials so long as they are suitable for the sample 30.

A breaking-up stick 20 is substantially composed of a breaking-up stick main body 21 and an O-ring 22, and is operatively inserted into the breaking-up tube 11 so as to be slidable and rotatable in a sealed manner. It is to be noted that the breaking-up stick 20 may not be rotatable relative to the breaking-up tube 11. The breaking-up stick 21 is made of plastic and comprises a handle 21a, a connecting section 21c and a sample pressing section 21d all of which have been integrally molded (e.g., injection molded). The handle 21a defines a circular column and is provided with knurls 21b thereon spaced equally apart along a circumferential direction (divided by 12 along a circumference in the drawing) so as to facilitate the rotating operation of the breaking-up stick 20 by an operator. It is to be noted that the knurls 21b may not be provided, and/or the handle 21a may be formed into other column-like bodies, such as polygonal column (not shown), that may be gripped easily by the operator. The connecting section 21c is a column-shaped body made up of four plates spaced equally apart along a circumferential direction. It is to be noted that the connecting section 21c may be formed into other polygonal column-shapes (not shown).

The pressing section 21d is a circular column having an outer diameter slightly smaller than the inner diameter of the cylindrical section 11e of the breaking-up tube 11, and is provided with a groove 21e extending along its circumference arranged on an outer surface in the vicinity of a top end thereof located in the sample side (lower end in the drawing). The O-ring 22 is fitted into the groove 21e, such that when the breaking-up stick 20 is inserted into the breaking-up tube 11, a pressing section 21d of the breaking-up stick 20 seals the cylindrical section 11e. The reason the O-ring 22 is used to seal the breaking-up tube 11 (cylindrical section 11e) resides in that a back-flow of the "mashed" sample 30 should be prevented by using the O-ring 22 thereby to seal the breaking-up tube 11, in order to ensure the safety of the operator and to prevent contamination of the surrounding environment (it is especially important in handling the morbific samples). It is to be noted that the pressing section 21d may not be provided with the O-ring 22, but in that case, the outer diameter of the pressing section 21d should be equal to the inner diameter of the cylindrical section 11e of the breaking-up tube 11, so that the back-flow of said "mashed" sample 30 can be prevented (when the pressing section 21d is made of elastic material, the outer diameter of the pressing section 21d may be slightly larger than the inner diameter of the cylinder section 11e).

Figure 2:
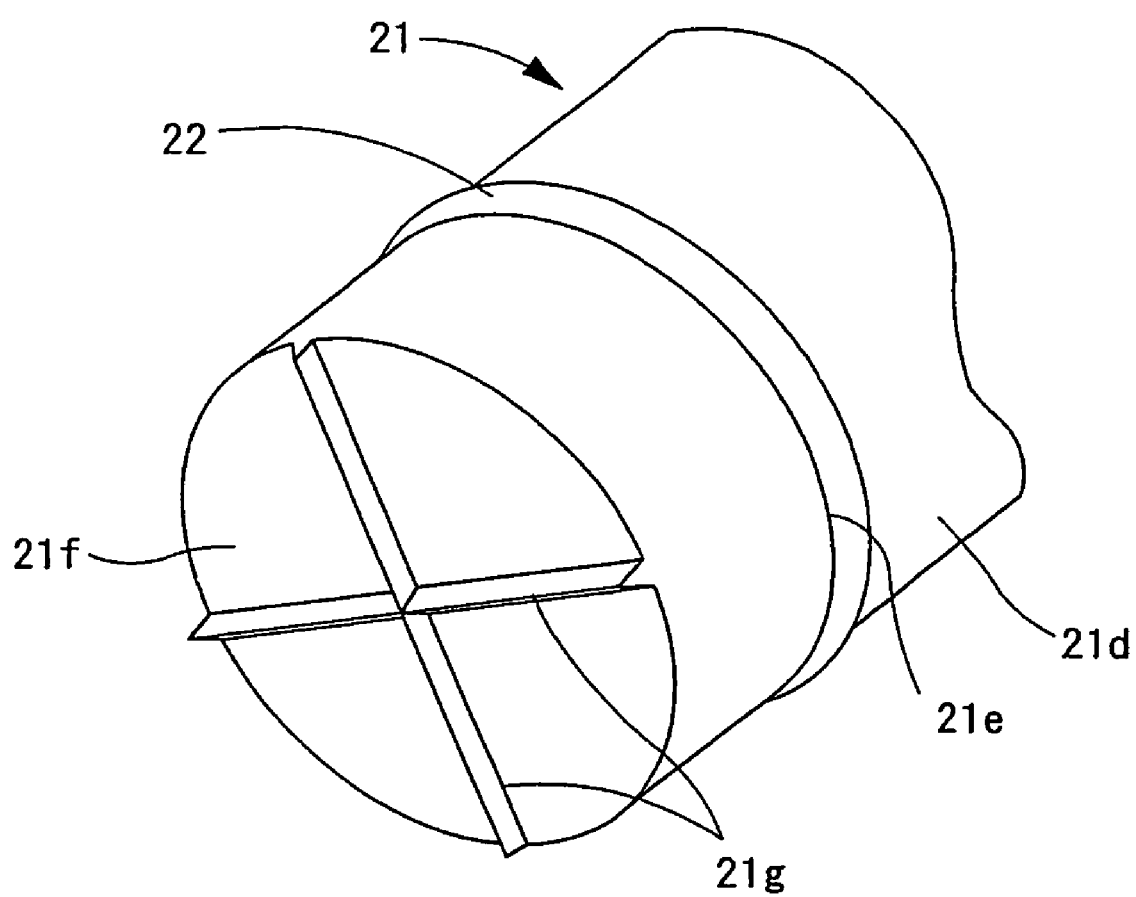
FIG. 2 is a perspective view of a bottom portion of a pressing member in FIG. 1 (First embodiment)

Four protrusions 21g are arranged in a lower end surface 21f of the pressing section 21d, and extend radially so as to cross at right angles with each other (i.e., dividing the end surface by four in the circumferential direction) as shown in FIG. 2. It is to be noted that any number of the protrusions 21g may be provided, or even the protrusions may not be provided.

It is to be noted that the breaking-up stick 20 may not be integrally molded, and/or may be made of any desired material other than plastic, and further it may be composed of the handle 21a and the pressing section 21d that are connected directly without interposing the connecting section 21c therebetween.

As described above, the sample breaking-up instrument of the present invention can be manufactured with reduced cost because of its simple structure, and accordingly it is inexpensive and therefore can be made disposable. Owing to those advantages, possible mixing among samples can be prevented, which could occur when the same instrument is used to "break-up" a plurality of samples (preventing mixing among samples is a prerequisite for conducting research as well as experiments).

Next, a sample breaking-up method using the sample breaking-up instrument 1 will be described with reference to FIGS. 1, 4 and 5.

A sample 30 is placed onto the filter 12 within the hole of the breaking-up tube 11 from the other opening end (upper end in FIG. 1), and the breaking-up stick 20 is operatively inserted into the hole from the same opening end so as to be slidable in a sealed manner. After that, as shown in FIG. 4, the breaking-up tube 11 is inserted into a sample recovery tube 40. This makes it possible that the "broken-up" sample 30 can be directly recovered into the recovery tube 40. It is to be noted that the recovery tube 40 need not necessarily be used, and in that case the "broken-up" sample may be collected into another collecting container.

Figure 4:
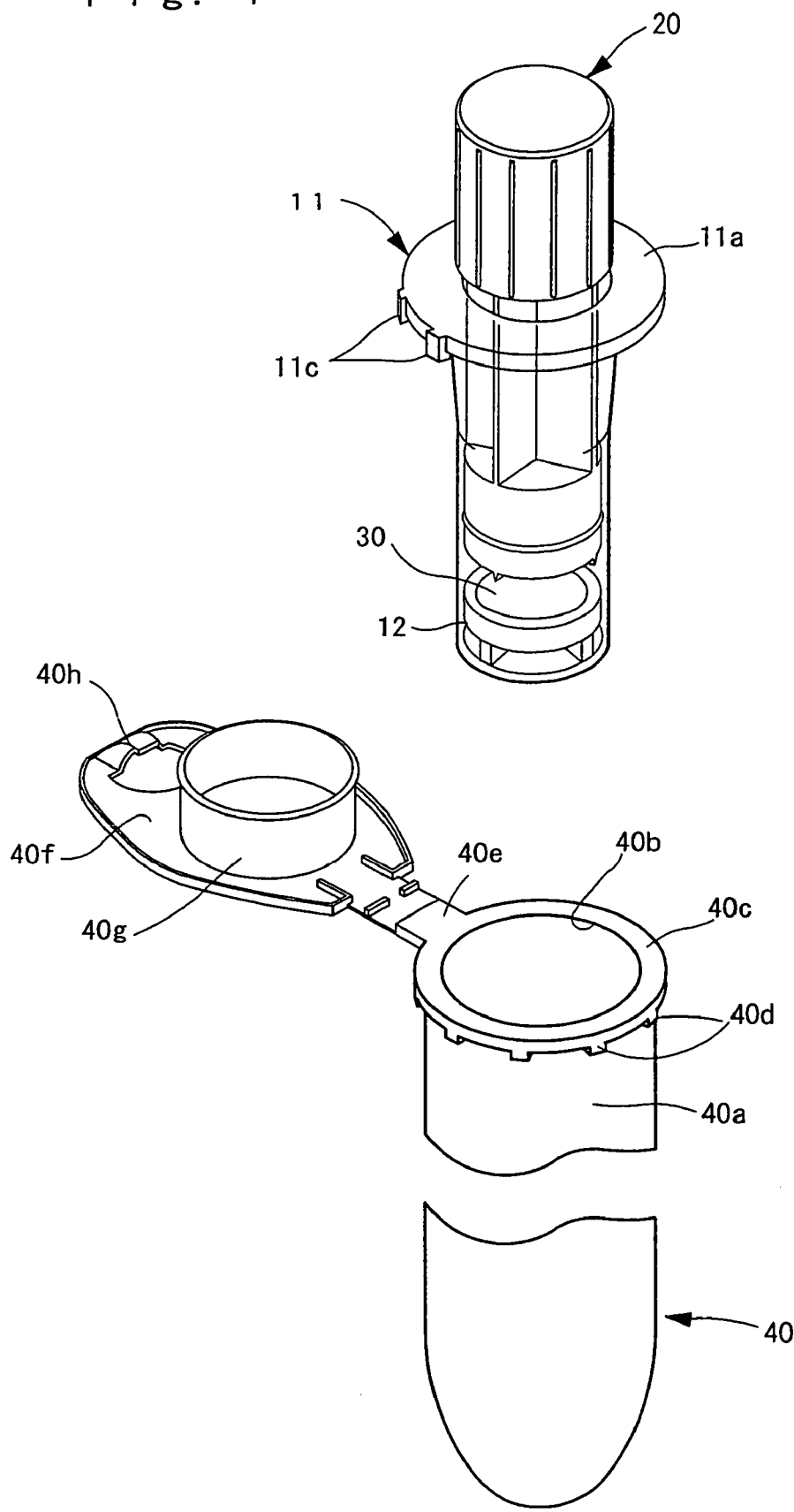
FIG. 4 is an exploded perspective view of a sample breaking-up instrument and a sample recovery tube (First embodiment)
Figure 5:
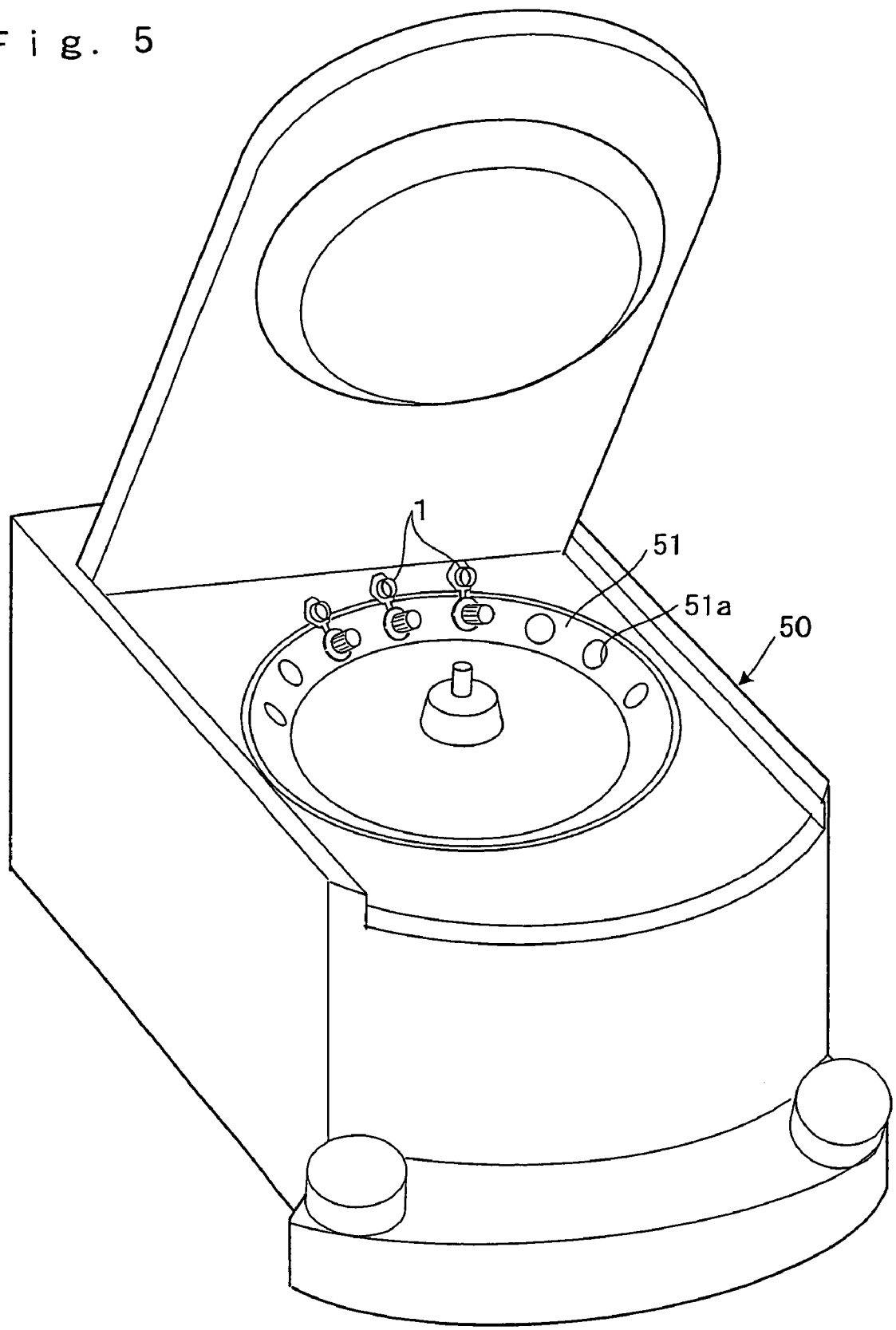
FIG. 5 is a perspective view of a centrifuge having a sample breaking-up instrument set therein (First embodiment).

In this illustrated embodiment, the recovery tube 40 substantially comprises a cylindrical tube main body 40a having a bottom and a ring-shaped flange 40c extending outward in the radial direction from its open end 40b as shown in FIG. 4, and it may be made of plastic and commercially available (e.g., 1.5 ml or 2 ml tube manufactured by Eppendorf Corp. or Treff AG Corp.). The flange section 40c is provided with a plurality of protrusions 40d on its lower surface so as to be equally spaced along its circumferential directions. A cap section 40f having a cylindrical sealing section 40g to be fitted into the open end 40b is attached to the flange 40c via a flexible connecting section 40e. The cap section 40f further has a hook section 40h, in which, when the cap section 40f is moved to a closed position, the hook section 40h is engaged with the flange section 40c thereby to be locked in its position.

It is to be noted that when the breaking-up tube 11 is inserted into the sample recovery tube 40, the breaking-up tube 11 comes into contact at its flange section 11a with the flange section 40c of the recovery tube 40, such that the flexible connecting section 40e of the recovery tube 40 may be positioned between the two claw-shaped fixing sections 11c and thereby the breaking-up tube 11 may be positioned and fixed relative to the sample recovery tube 40. At that time, the cap section 40f of the recovery tube 40 is not in its closed position.

Subsequently, the breaking-up stick 20 is pressed, while being rotated with respect to the filter 12, to thereby "mash" the sample 30 (hereinafter referred to as the "mashing process" in certain cases). It is to be noted that although this "mashing process" is especially effective to improve the "breaking-up" efficiency (the recovery rate of the "broken-up" sample) when relatively hard samples, such as brain tissue and liver tissue, are broken-up, this "mashing process" may be eliminated (see "Experiment 1", described later).

After the sample 30 has been "mashed" sufficiently, the commercially available centrifuge 50 is used to "break-up" the sample 30. That is, the breaking-up tube 11 as it is inserted in the sample recovering tube 40 is inserted from its lower end into a tube holding hole 51a of a rotary table 51 of the centrifuge 50, and the rotary table 51 is rotated by a desired number of times to exert the centrifugal force onto the breaking-up stick 20 so that the breaking-up stick 20 can press the sample 30 against the filter 12.

As it is, the sample 30 is forced to pass through the filter 12 to be "broken-up" and recovered into the recovery tube 40 (after recovery, the cap section 40f of the recovery tube 40 is moved into its closed position appropriately). It is to be noted that while the breaking-up tube 11 is being set in the centrifuge 50, there is no chance that the "broken-up" sample 30 leaks out of the recovery tube 40 (for example, an axial line direction of the tube holding hole 51a of the centrifuge 50 is inclined downward at an angle from a plane of rotation of the rotary table 51, so that said leakage can be prevented), but additionally a seal means (for example, an O-ring disposed at a predetermined location external to the breaking-up tube 11 (not shown)) may be disposed between the breaking-up tube 11 and the recovery tube 40.

According to the sample breaking-up instrument 1 of the present invention, since the centrifuge 50 can be used to "break-up" the sample 30, it can simplify the operation as compared to the potter-type homogenizer that requires the operator to manually "break-up" the sample. Further, since the centrifuge 50 can apply the centrifugal separation to a plurality of recovery tubes 40 all at once, a plurality of samples 30 can be simultaneously broken-up and thereby the sample breaking-up instrument 1 can improve the working efficiency (or the task processing rate) as compared to the potter-type homogenizer and the rotor-stator system homogenizer of the prior art, which require that samples should be "broken-up" one by one.

It is to be noted that the centrifuge 50 is preferably equipped with a cooling function. This can help prevent the sample from being heat-modified resultant from frictional heat and the like that could be generated during the "breaking-up", while at the same time it helps prevent decomposition due to endogenous enzyme and allows a target substance to be extracted from the "homogenized" sample 30 without giving any damage thereto.

Alternatively, the centrifuge 50 need not necessarily be used, and in that case the breaking-up stick 20 may be pressed by a mechanical force, for example, by the operator pressing the breaking-up stick 20 directly with his/her finger(s).

[Experiment 1]

The QIA shredder of the prior art and a sample breaking-up instrument of the present invention were used respectively to determine a breaking-up efficiency (a recovery rate of the "broken-up" sample) of a bovine cerebral medulla representing a biological sample, and the results of this experiment are shown and compared in Table 1. Specifically, Table 1 shows the results of the comparison between the recovery rate of the sample by the QIA shredder, in which the sample was "broken-up" by forcing it to pass through the filter exclusively by means of the centrifugal force exerted on the sample itself without "mashing" the sample with the breaking-up stick, and the recovery rate of the sample by the sample breaking-up instrument of the present invention, in which the sample was "broken-up" by utilizing not only the centrifugal force exerted on the sample itself but also the centrifugal force exerted on the breaking-up stick to thereby force the sample to pass through the filter. It is to be noted that the experiment which utilized the sample breaking-up instrument of the present invention was conducted under two conditions: in one condition where the "mashing process" was previously carried out and in the other condition where the "mashing process" was not carried out.

Herein, both of the experiments using the QIA shredder and the sample breaking-up instrument of the present invention employed a centrifuge for the Eppendorf-type microtube, in which the sample was rotated for one minute at a revolving rate of 10000 rpm to 15000 rpm.

In the same table, seen from the left (also applied to the description below), values listed in the first column "Sample weight" indicate the measured values of the samples that were actually used in the experiment by the QIA shredder, values in the second column "Recovery weight" indicate respective weights of the samples that passed through the filter and then recovered in the experiment by the QIA shredder, and values listed in the third column "Recovery rate" indicate the ratios defined by dividing said "Recovery weight" by said "Sample weight".

On the other hand, respective values listed in respective columns, from the fourth to the ninth columns, indicate the results of experiment that were obtained under the different conditions by using the sample breaking-up instrument of the present invention. That is, those values listed in respective columns, from the fourth to the sixth columns, represent the values similar to those listed in said first to said third columns specifically for the case where the "mashing process" was not previously applied, but the breaking-up stick was inserted into the breaking-up tube so that not only the centrifugal force exerted on the sample itself but also the centrifugal force exerted on the breaking-up stick were utilized to "break-up" the sample, while those values listed in respective columns, from the seventh to the ninth columns, represent the values similar to those listed in said first to said third columns specifically for the case where the "mashing process" was previously applied and also the breaking-up stick was inserted into the breaking-up tube to "break-up" the sample by the centrifugal force exerted on the breaking-up stick.

According to the results of the experiment, firstly in the comparison between the recovery rate using the QIA shredder and the recovery rate for the case using the sample breaking-up instrument of the present invention without applying the "mashing process", the recovery rate with the QIA shredder is around 10%, whereas the recovery rate with the sample breaking-up instrument of the present invention is substantially around 37 to 53% (see Table 1).

That is, since using the sample breaking-up instrument of the present invention allows the sample to be "broken-up" by not only the centrifugal force exerted on the sample itself but also the centrifugal force exerted on the breaking-up stick, it is possible to improve the recovery rate (breaking-up efficiency) of the sample dramatically as compared to the prior art (QIA shredder).

Subsequently, in comparison between the recovery rate for the case using the sample breaking-up instrument of the present invention without applying the "mashing process" and the recovery rate for the case using the same instrument with applying the "mashing process", the recovery rate without the "mashing process" is approximately 37 to 53%, whereas the recovery rate with the "mashing process" is approximately 46 to 59% (see Table 1).

This means that applying the "mashing process" in addition can improve the recovery rate (breaking-up efficiency) of the sample.

TABLE 1

| | QIA shredder | | | Sample breaking-up instrument of the present invention | | | | |
| --- | --- | --- | --- | --- | --- | --- | --- | --- |
| | | | | Without "mashing process" | | | With "mashing process" | | |
| Sample weight (mg) | Recovery weight (mg) | Recovery rate (%) | Sample weight (mg) | Recovery weight (mg) | Recovery rate (%) | Sample weight (mg) | Recovery weight (mg) | Recovery rate (%) |
| 109 | 15.1 | 13.9 | 131 | 70.5 | 53.8 | 131 | 72.8 | 55.6 |
| 90 | 10 | 11.1 | 107 | 55.2 | 51.6 | 107 | 62.7 | 58.6 |

TABLE 1-continued

| | | | Sample breaking-up instrument of the present invention | | | | | |
|---|---|---|---|---|---|---|---|---|
| QIA shredder | | | Without "mashing process" | | | With "mashing process" | | |
| Sample weight (mg) | Recovery weight (mg) | Recovery rate (%) | Sample weight (mg) | Recovery weight (mg) | Recovery rate (%) | Sample weight (mg) | Recovery weight (mg) | Recovery rate (%) |
| 94 | 9.3 | 9.9 | 130 | 55.2 | 42.5 | 130 | 60.7 | 46.7 |
| 106 | 10.9 | 10.3 | 90 | 34.1 | 37.9 | 90 | 43.9 | 48.8 |
| 90 | 7.4 | 8.2 | 90 | 36 | 40.0 | 90 | 45.1 | 50.1 |
| 106 | 7.4 | 7.0 | 130 | 70 | 53.9 | 130 | 77.3 | 59.5 |

[Experiment 2]

Secondly, Table 2 shows the result from an experiment in which a sample breaking-up instrument of the present invention was used to "break-up" a sample other than a biological sample.

The background of the experiment is as detailed below. That is, to further analyze the protein that has been separated in the SDS polyacrylamide gel electrophoresis, it is necessary to extract the protein from the gel. In spite of the fact that the gel needs to be broken-up to increase the efficiency of the extraction of the protein from the gel, there has been so far no suitable method for the fragmentation.

A detailed description of the experiment will now be provided.

Bovine serum albumin (BSA) prepared as protein is dissolved in 12% polyacrylamide solution to make 0.7% solution of BSA, and the resultant solution is polymerized by using TEMED and ammonium persulfate in the slab gel generator (thickness of 0.75 mm). After the acrylamide has sufficiently polymerized and gelled, the gel is cut into portions precisely such that each one weighs 180 mg. One of the cut-out portions of the gel is directly inserted into the Eppendorf tube, while another portion of the gel is "broken-up" by using the sample breaking-up instrument of the present invention and thus "broken-up" gel is recovered into the recovery tube. After each portion of the gel is added with distilled water by a volume of 0.5 ml and shaken, an amount of the BSA having dissolved into the distilled water is determined based on the ultraviolet ray absorption (280 nm).

Table 2 shows the extraction rates of the BSA from the respective gels. That is, in the same table, seen from the top (also applied to the description below), values listed in the first row indicate extraction time (time elapsed), values listed in the second row indicate the extraction rate of the BSA from the gel that has not been "broken-up", and values in the third row indicate the extraction rate of the BSA from the gel that has been "broken-up" by using the sample breaking-up instrument of the present invention. It is to be noted that the extraction rate was calculated based on the ultraviolet ray absorption of a solution prepared by adding 0.5 ml of distilled water to the 0.7% BSA solution that had not been encapsulated in the gel, which was taken as a reference indicated by 100%.

According to the result of the experiment, said not "broken-up" gel took two hours or longer to gain 60% of extraction rate, while the gel "broken-up" by the sample breaking-up instrument of the present invention successfully achieved a 60% or higher rate of extraction of the BSA after 5 minutes (see Table 2). Further, in the comparison of the final extraction rate measured after one day having been fully elapsed, said not "broken-up" gel exhibits a 62% of extraction rate, while the gel "broken-up" by using the sample breaking-up instrument of the present invention exhibits a 72% extraction rate, indicating obviously that the gel "broken-up" by the sample breaking-up instrument of the present invention has a higher rate of extraction (see Table 2).

This means that also in the case of a sample other than a biological sample, the sample breaking-up instrument of the present invention can "break-up" the sample in a simple and efficient manner suitably in response to a requirement for each different purpose.

TABLE 2

| | Extraction time | | | | |
|---|---|---|---|---|---|
| | 5 min. | 30 min. | 2 hr. | 4 hr. | 24 hr. |
| Extraction rate for not-broken-up condition (%) | 30 | 33 | 60 | 62 | 62 |
| Extraction rate for Broken-up condition (%) | 62 | 64 | 72 | 72 | 72 |

It will be apparent to those skilled in the art that various modifications and variations would be made to a sample breaking-up instrument and a sample breaking-up method described above, without departing from the scope or the inventive concept of the present invention. Other embodiments of the present invention will become obvious to those skilled in the art from the consideration given to the specification as well as the embodiments disclosed in the specification of the present invention. This specification and embodiments are intended to be considered simply by way of example.

The attached drawings are included in this specification as a part thereof, and are helpful, in conjunction with the detailed description, to show schematically the preferred embodiments of the present invention and to illustrate the principle of the present invention.

INDUSTRIAL APPLICABILITY

The present invention is applicable to an instrument and a method for breaking-up a sample safely and efficiently. It is also applicable to a fragmentation of a relatively hard sample, such as brain tissue and liver tissue. Further, the present invention is applicable to the purpose for breaking-up a sample that could be modified easily by a generated heat or that could contaminate the surroundings. The present invention may be further applicable to a breaking-up instrument having such a requirement that a sample to be broken-up is highly toxic and once the sample is broken-up in this breaking-up instrument, the used instrument could not be reused and must be disposable.

The invention claimed is:

1. An instrument for breaking-up a sample, comprising:
a cylindrical body having a through hole opening in both ends thereof;
a filter member installed in one end of said cylindrical body within said through hole; and
a pressing member to be operatively inserted into said hole of said cylindrical body from the other end thereof so as to be slidable therethrough in a sealed manner, wherein, a centrifugal force is exerted on said pressing member so that said pressing member presses said sample placed between said pressing member and said filter member against said filter member and thereby said sample is forced to pass through said filter member and is thus broken-up, in which said pressing member is provided with a protrusion extending radially on an end surface thereof to face to the sample, wherein said pressing member is able to be pressed while being rotated with respect to said filter member so that said sample is mashed before being forced to pass through said filter member by said force, in which said cylindrical body is provided with a drop-out stop for preventing said filter member from dropping out of said cylindrical body, in the vicinity of the opening located in said one end thereof, said drop-out stop comprising two members extending diametrically so as to cross at right angles to each other.

2. A sample breaking-up instrument in accordance with claim 1, in which said pressing member is provided with a groove extending circumferentially on an outer surface thereof in the vicinity of its top end located in the sample side, and an O-ring is fitted in said groove.

3. A sample breaking-up instrument in accordance with claim 1, in which said filter member has a plurality of through holes, each having a diameter of a cross section orthogonal to an axis in a range of 50 to 200 micrometers.

4. A sample breaking-up instrument in accordance with claim 1, in which said filter member defines a plate having a thickness in a range of 1 to 3 millimeters.

5. A method for breaking-up a sample, comprising the steps of:
preparing a cylindrical body equipped with a filter member in one end of a through hole formed therein so as to open in both ends;
placing said sample into said hole of said cylindrical body from the other opening end thereof;
operatively inserting a pressing member into said hole of said cylindrical body from said other opening end thereof so as to be slidable therethrough in a sealed manner;
exerting a centrifugal force on said pressing member so that said pressing member presses said sample against said filter member to thereby force said sample to pass through said filter; and
said pressing member is provided with a protrusion extending radially on an end surface thereof so as to face to a sample, and said method further comprises a step of mashing said sample by pressing said pressing member while rotating it with respect to said filter member before exerting the centrifugal force on said pressing member.

* * * * *